United States Patent [19]
Yates

[11] Patent Number: 5,716,366
[45] Date of Patent: *Feb. 10, 1998

[54] HEMOSTATIC SURGICAL CUTTING OR STAPLING INSTRUMENT

[75] Inventor: David C. Yates, West Chester, Ohio

[73] Assignee: Ethicon Endo-Surgery, Inc., Cincinnati, Ohio

[*] Notice: The term of this patent shall not extend beyond the expiration date of Pat. No. 5,624,452.

[21] Appl. No.: 701,620

[22] Filed: Aug. 22, 1996

Related U.S. Application Data

[63] Continuation of Ser. No. 418,750, Apr. 7, 1995, Pat. No. 5,624,452.

[51] Int. Cl.$^6$ .................................................. A61B 17/00
[52] U.S. Cl. .............................. 606/139; 606/27; 606/45; 227/19; 227/175.1
[58] Field of Search .................................. 606/27–29, 32, 606/41, 45–47, 51–52, 139, 142, 143, 1, 205–208; 227/901, 19, 175.1–182.1

[56] References Cited

U.S. PATENT DOCUMENTS

| | | |
|---|---|---|
| 2,031,682 | 2/1936 | Wappler et al. . |
| 3,768,482 | 10/1973 | Shaw . |
| 3,826,263 | 7/1974 | Cage et al. . |
| 4,655,216 | 4/1987 | Tischer . |
| 4,848,337 | 7/1989 | Shaw et al. . |
| 5,122,137 | 6/1992 | Lennox .................. 606/40 |
| 5,147,356 | 9/1992 | Bhatta .................. 606/142 |
| 5,207,691 | 5/1993 | Nardella ................ 606/142 |
| 5,306,280 | 4/1994 | Bergen et al. .......... 606/143 |
| 5,336,221 | 8/1994 | Anderson ............... 606/27 |
| 5,364,389 | 11/1994 | Anderson .............. 606/127 |
| 5,389,098 | 2/1995 | Tsuruta et al. ......... 606/41 |
| 5,417,687 | 5/1995 | Nardella et al. ....... 606/32 |
| 5,445,638 | 8/1995 | Rydell et al. .......... 606/51 |
| 5,458,598 | 10/1995 | Feinberg et al. ....... 606/205 |

FOREIGN PATENT DOCUMENTS

| | | | |
|---|---|---|---|
| WO 93/08754 | 5/1993 | WIPO | A61B 17/36 |
| WO 94/24949 | 11/1994 | WIPO | A61B 17/36 |
| WO 94/24951 | 11/1994 | WIPO | A61B 17/39 |

OTHER PUBLICATIONS

Radio Frequency Energy and Impedance Feedback, Paul C. Nardella, SPIE vol. 1068, Catheter–Based Sensing and Imaging Technology (1989).

*Primary Examiner*—Jeffrey A. Schmidt

[57] ABSTRACT

A hemostatic surgical instrument is provided for coagulation, cauterization and/or welding of tissue especially in the performance of endoscopic procedures. The instrument compresses the tissue between interfacing surfaces of first and second elements. A preferred application of the invention is in a cutting instrument wherein a hemostatic line is formed along a cut line using therapeutic heat energy. Surgical fasteners, for example, staples may be also included in the instrument.

6 Claims, 12 Drawing Sheets

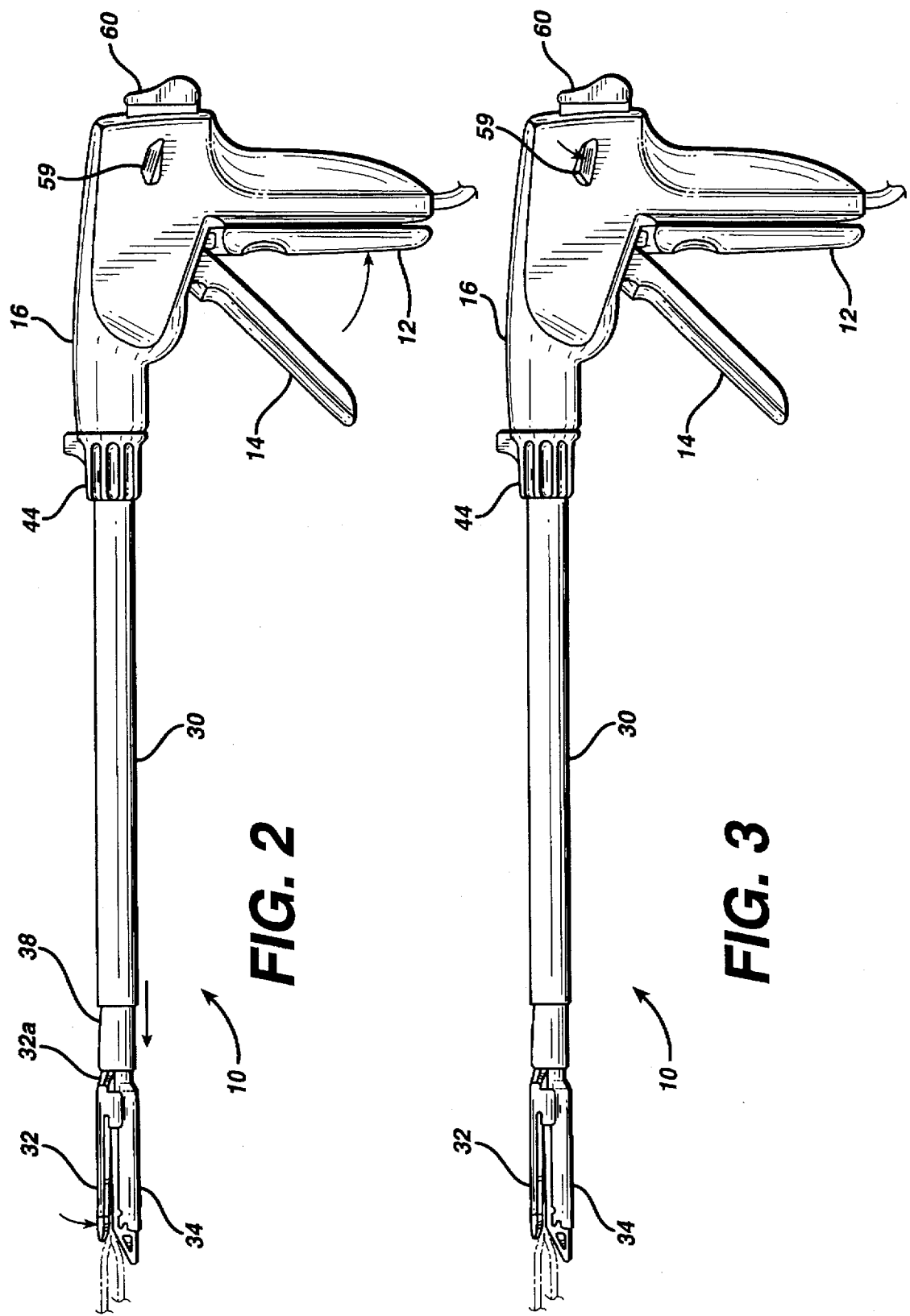

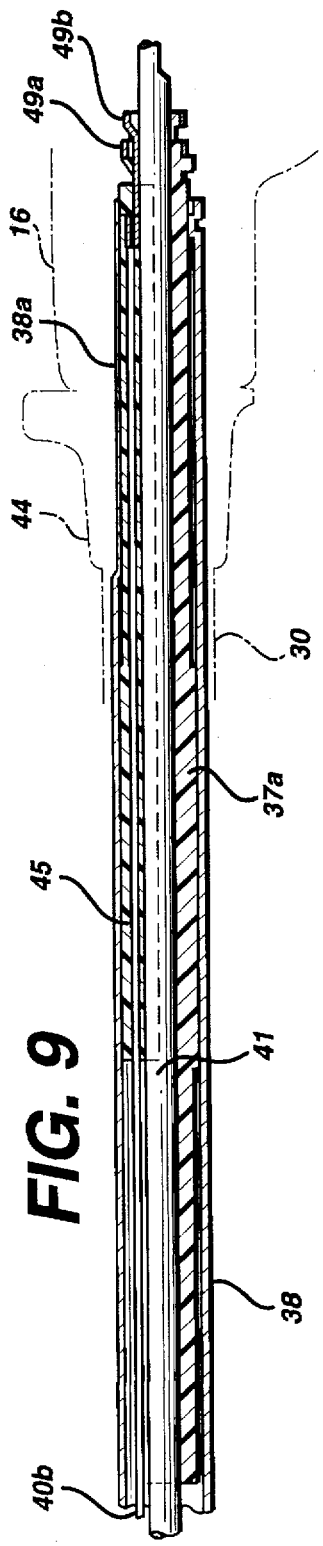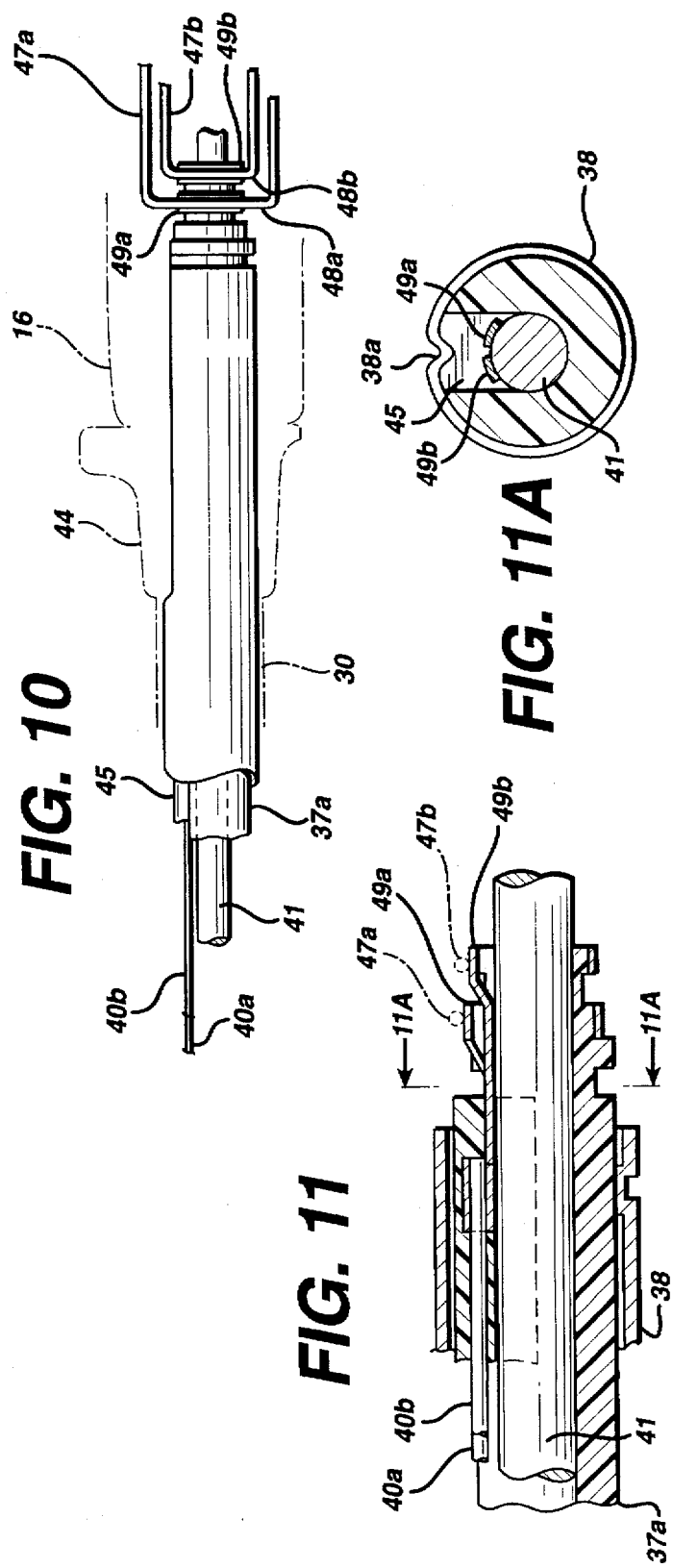

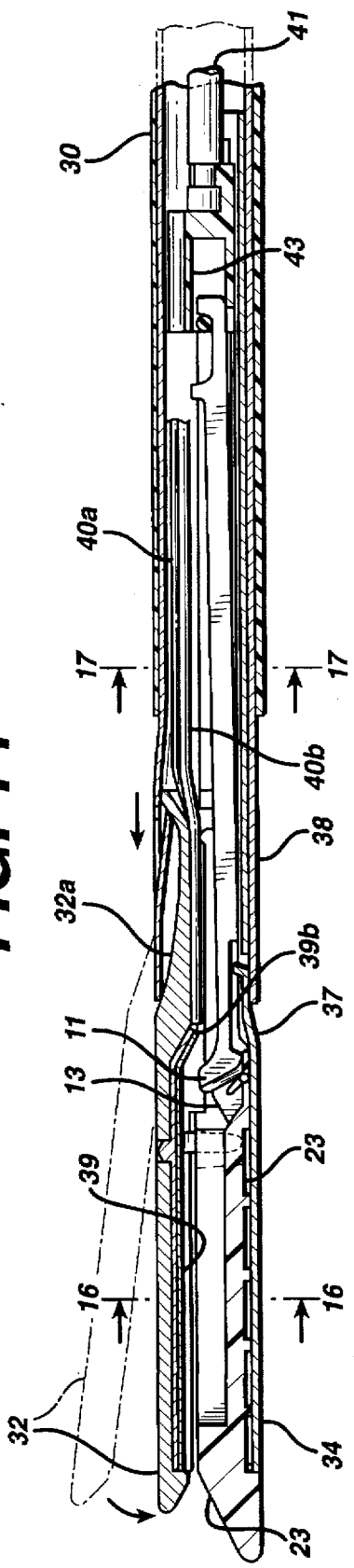
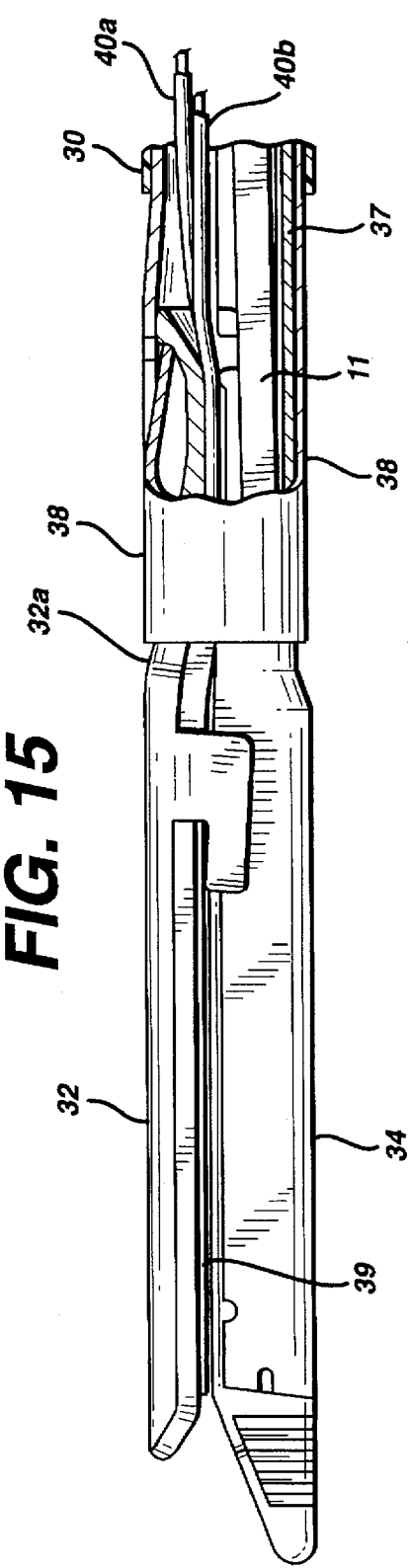
FIG. 14
FIG. 15

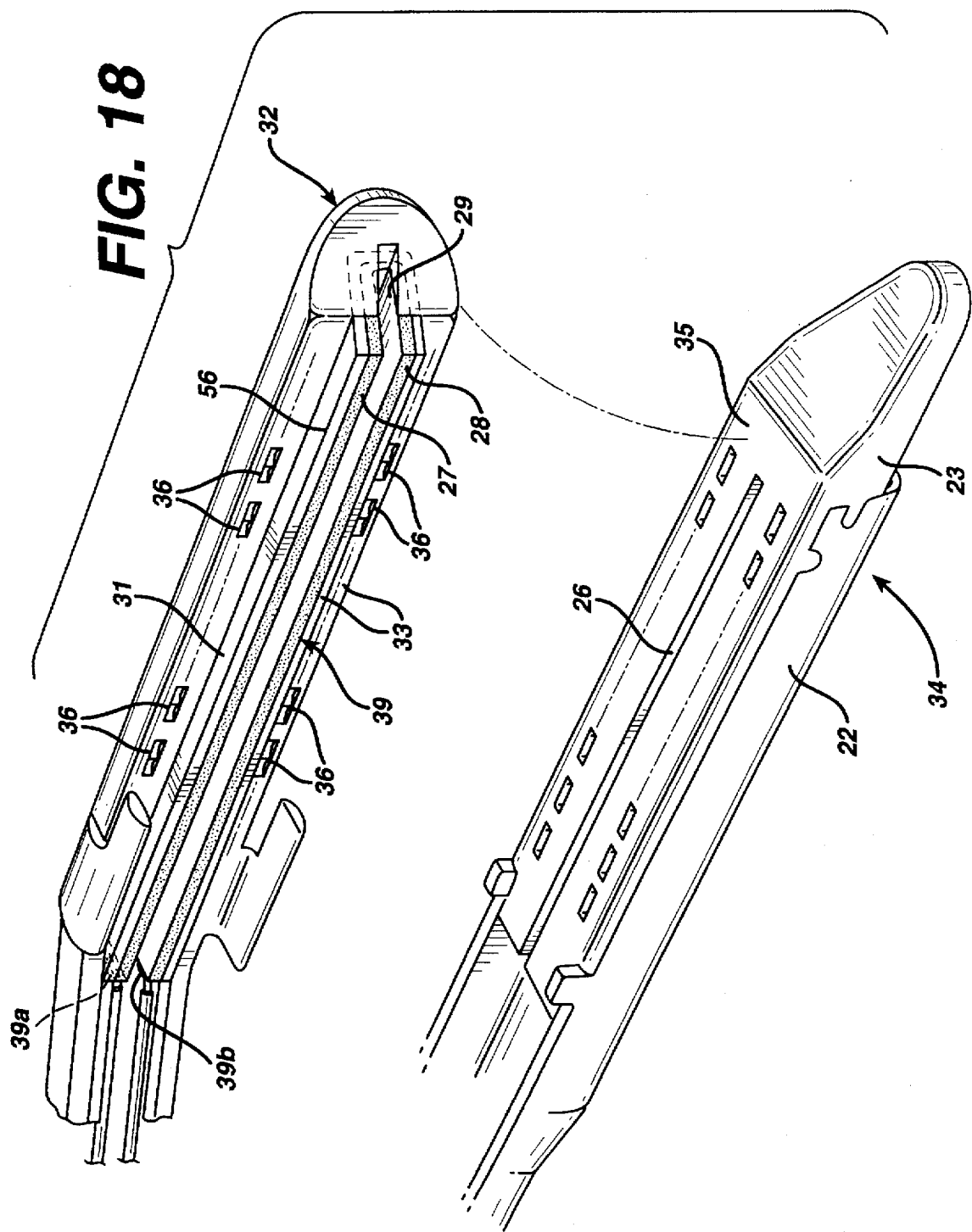

HEMOSTATIC SURGICAL CUTTING OR STAPLING INSTRUMENT

This is a continuation of application Ser. No. 08/418,750, filed Apr. 7, 1995 now U.S. Pat. No. 5,624,452, which is hereby incorporated by reference.

FIELD OF THE INVENTION

This invention relates to an electrosurgical instrument for treating tissue with heat in the performance of surgical procedures, especially endoscopic procedures.

BACKGROUND OF THE INVENTION

Surgical procedures requiring cutting of tissue can cause bleeding at the site of the cutting. Various techniques have been adapted to control bleeding with varying degrees of success such as, for example, suturing, applying clips to blood vessels, and stapling, as well as electrocautery and other tissue heating techniques. Advances in tissue joining or welding, tissue repair and wound closure also have permitted surgical procedures previously not possible or too risky.

Surgical staplers have been used for tissue security, joining, and approximation, and to provide hemostasis in conjunction with tissue cutting. Such devices include, for example, linear and circular cutting and stapling instruments.

Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows. Hemostasis is used herein to mean generally the arresting of bleeding including by coagulation, cauterization and/or tissue joining or welding.

Devices using heating elements have been described, for example, to heat surgical cutting blades to provide hemostasis when cutting tissue with a blade. This type of device provides only limited control of tissue manipulation, coagulation, and/or thermal damage.

It is therefore desirable to provide a surgical device with a hemostatic heating element which provides control of tissue heating or treatment within a controlled zone.

SUMMARY OF THE INVENTION

Accordingly, the present invention provides hemostatic clamping device which enables grasping tissue while applying heat energy to the tissue.

One embodiment of the invention provides a surgical device that has an end effector with opposing interfacing surfaces for engaging tissue therebetween. Preferably a clamping device with a mechanical cutting element is provided, arranged to divide tissue that has been or that is adjacent to tissue that has been coagulated by the heating elements of the clamping device.

In one embodiment a clamping, and cutting device is provided where the heating element is associated with the clamping elements, i.e., is located on one or more of the interfacing surfaces. In another embodiment the heating element is associated with the cutting element. In this embodiment the clamping element holds tissue while tissue is cut and coagulated with a heated knife blade. In these embodiments, the heating element preferably provides a hemostatic means for providing a line of coagulation along or lateral to a cutting path of the cutting element for dividing tissue.

It is another object of the invention to provide a hemostatic instrument having one or more elongated or bar heating elements. In one such embodiment, the heating element comprises first and second elongated elements each on opposite sides and lateral to a cutting path for a cutting element. The elongated elements provide hemostatic lines adjacent to the path of the cutting element.

In another embodiment, therapeutic heat energy is applied in conjunction with application of one or more tissue fasteners such as, for example, staples, clips, absorbable fasteners etc., using an applier to apply the fastener, such as a driver to drive staples into tissue.

In one such embodiment, the hemostatic device is incorporated into a linear cutter similar to a linear cutting mechanical stapler. In this embodiment the hemostatic device preferably comprises two elongated heating bars and a slot for a cutting means to cut tissue engaged by the end effector of the device. One or more rows of staples is provided on each side of the slot and bars to provide mechanical tissue security or approximation during the healing process. Operation of linear cutting and stapling instruments are known in the art and are discussed, for example, in U.S. Pat. Nos. 4,608,981 and 4,633,874 incorporated herein by reference. Other cutting and stapling instruments may be used as well, such as, for example, an interluminal circular cutting instrument.

In another embodiment, the coagulation is completed prior to any mechanical cutting, i.e., actuation of the cutting means. An indicator, e.g., a temperature indicator, communicates to the user that the tissue has been heated, coagulated, cauterized, or otherwise treated to a desired or predetermined degree. Once tissue is coagulated, the cutting element may be actuated to cut between the elongated bar electrodes while the rows of staples are applied to the tissue.

These and other objects of the invention will be better understood from the following attached Detailed description of the Drawings, when taken in conjunction with the Detailed Description of the invention.

DETAILED DESCRIPTION OF THE DRAWINGS

FIG. 2 is a side elevational view of the embodiment of FIG. 1 shown in a closed, clamped position, before cutting or stapling;

FIG. 3 is a side elevational view of the embodiment of FIG. 2 shown as heat energy is applied to tissue;

FIG. 9 is a longitudinal cross-sectional view of the intermediate portion of the instrument;

FIG. 10 is an elevational view of the proximal end of the intermediate portion showing the contact of the wireforms to their respective contact positions;

FIG. 11 is an enlarged cross-sectional view of the proximal end of the intermediate portion of the instrument;

FIG. 11a is a transverse cross sectional view taken along the lines 11a—11a of FIG. 11.

FIG. 14 is a longitudinal cross-sectional view of the distal end of the instrument of FIG. 1 shown in a closed and clamped position;

FIG. 15 is an enlarged partial cross-sectional view of the distal portion of FIG. 13;

FIG. 18 illustrates a perspective view of the end effector.

DETAILED DESCRIPTION OF THE PREFERRED EMBODIMENTS

Figure 1:
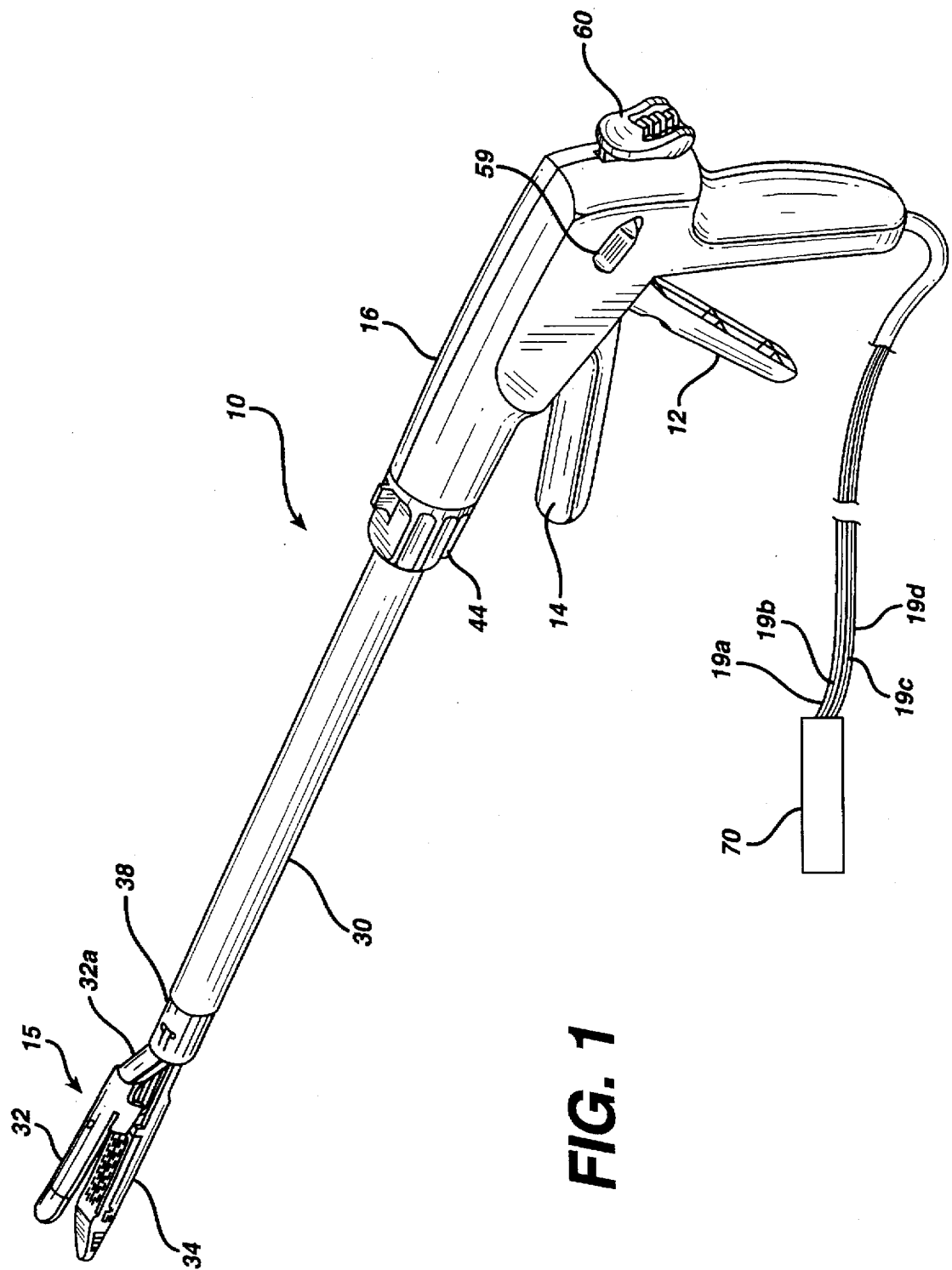
FIG. 1 is a perspective view of an endoscopic surgical instrument of one embodiment of the present invention.
Figure 4:
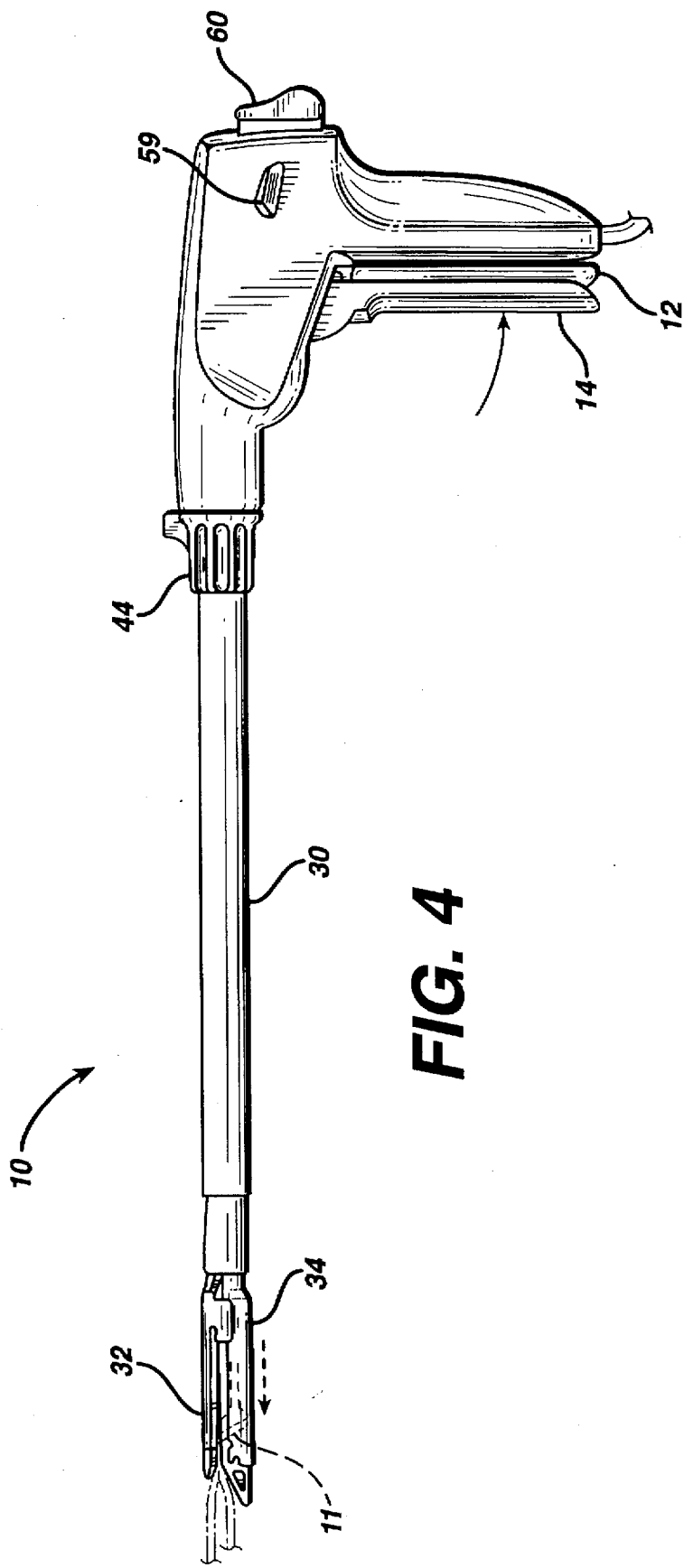
FIG. 4 is a side elevational view similar to FIG. 3 shown after heat energy has been applied and the tissue has been stapled and cut.
Figure 5:
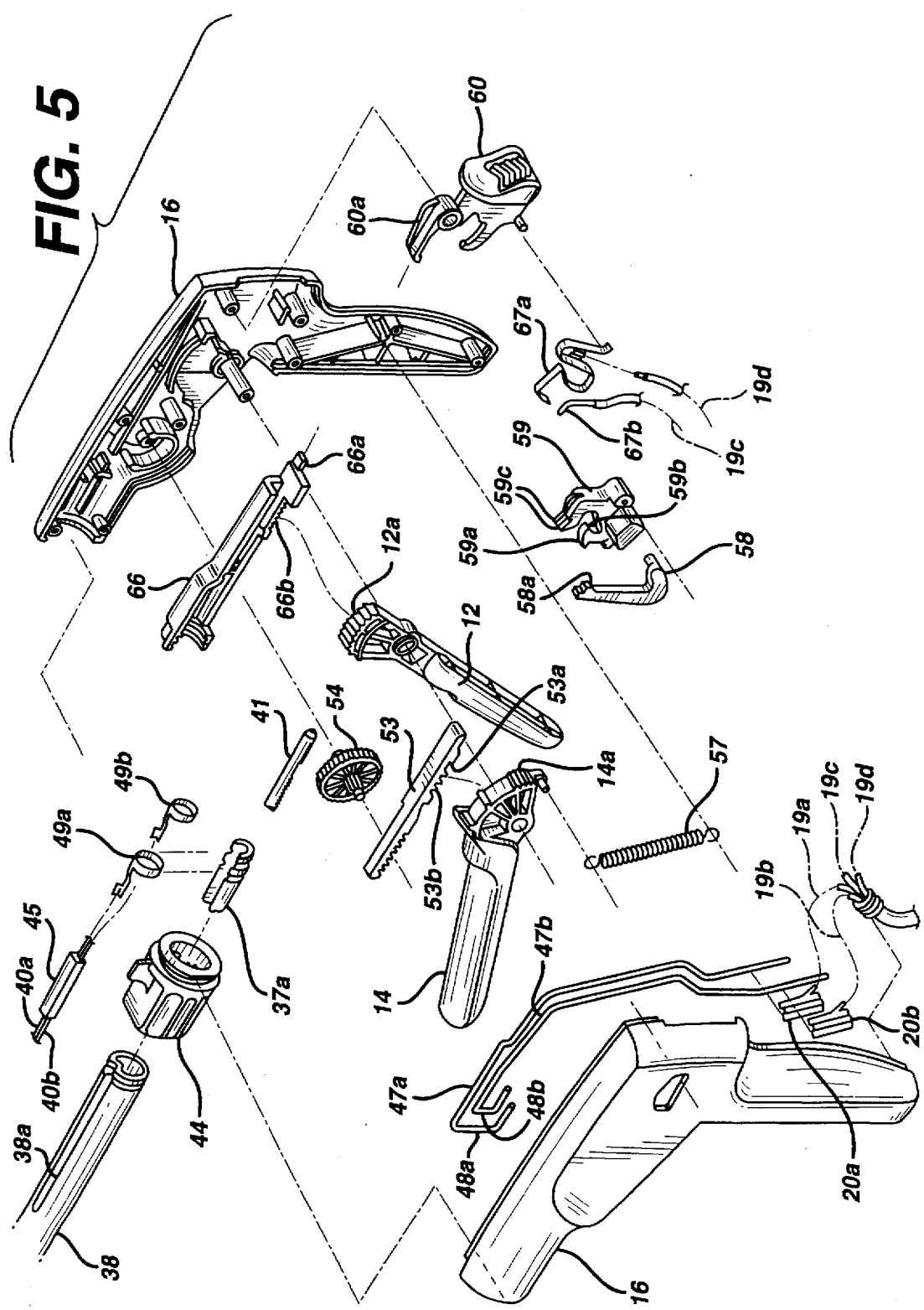
FIG. 5 is an exploded perspective view of the proximal handle portion of the instrument of FIG. 1.
Figure 6:
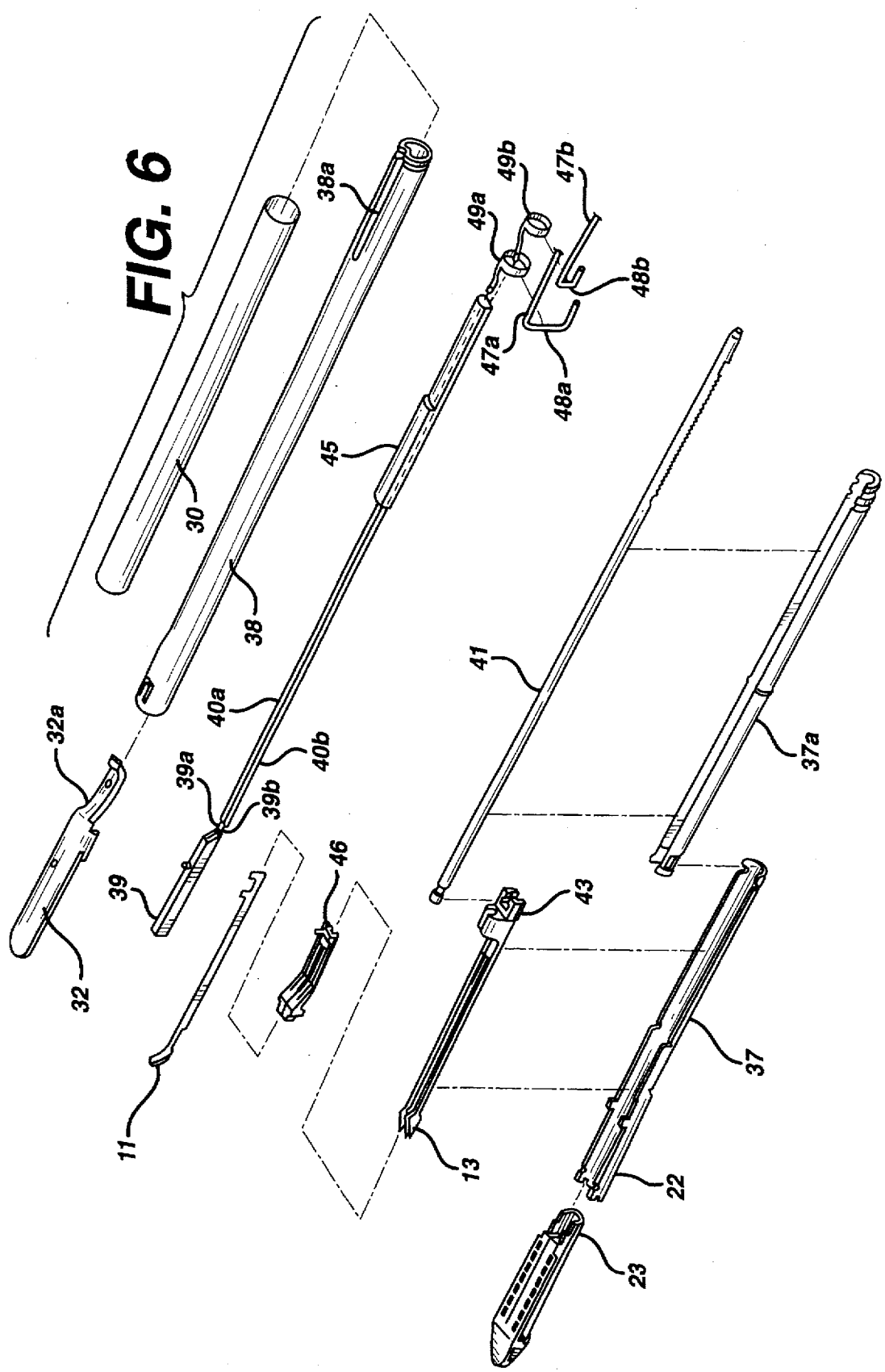
FIG. 6 is an exploded perspective view of the intermediate and distal portion of the instrument of FIG. 1.
Figure 7:
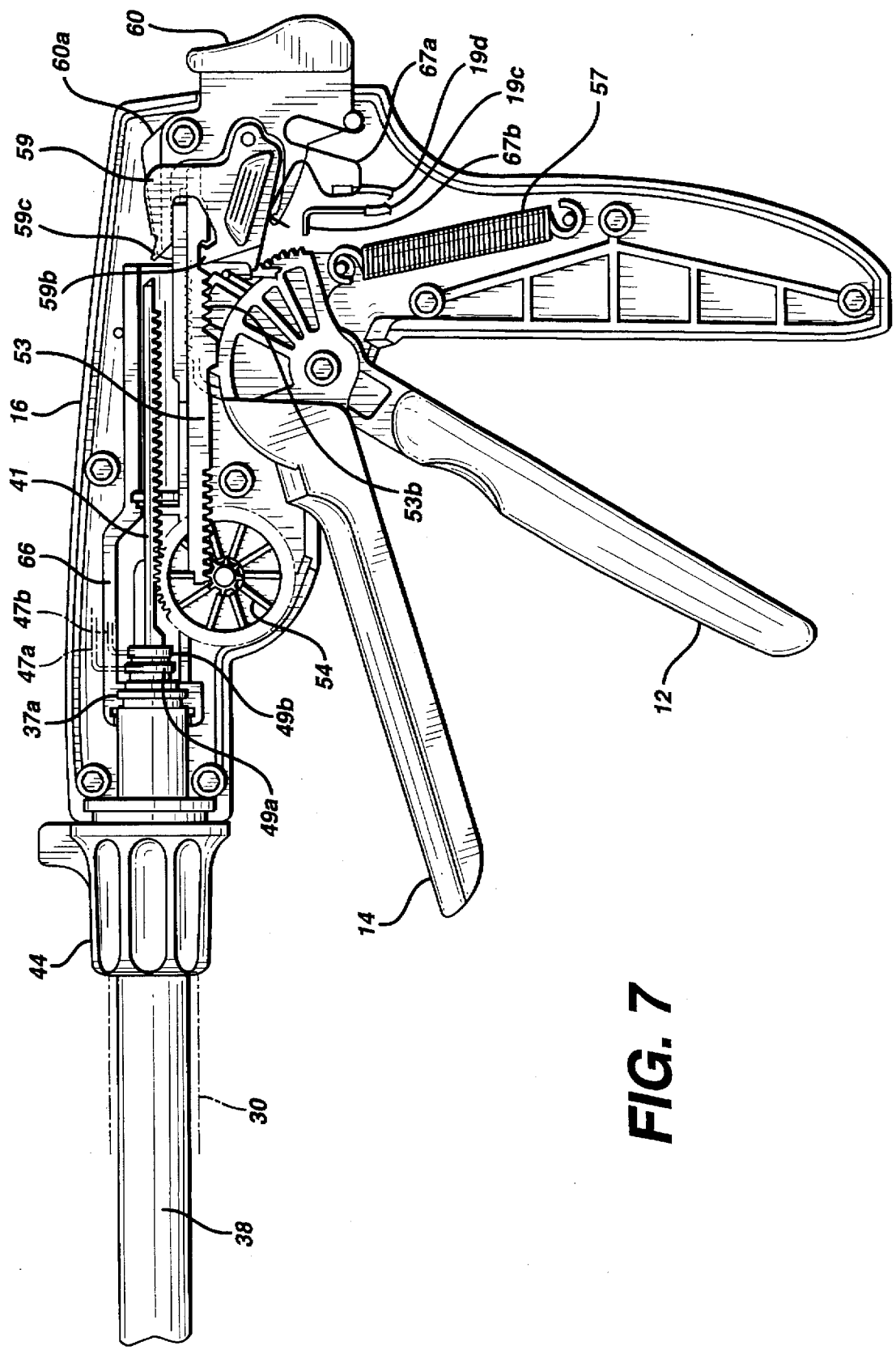
FIG. 7 is a side elevational view of the proximal handle portion in a first, open position of the instrument of FIG. 1, shown with the left side handle cover and wireforms removed.
Figure 8:
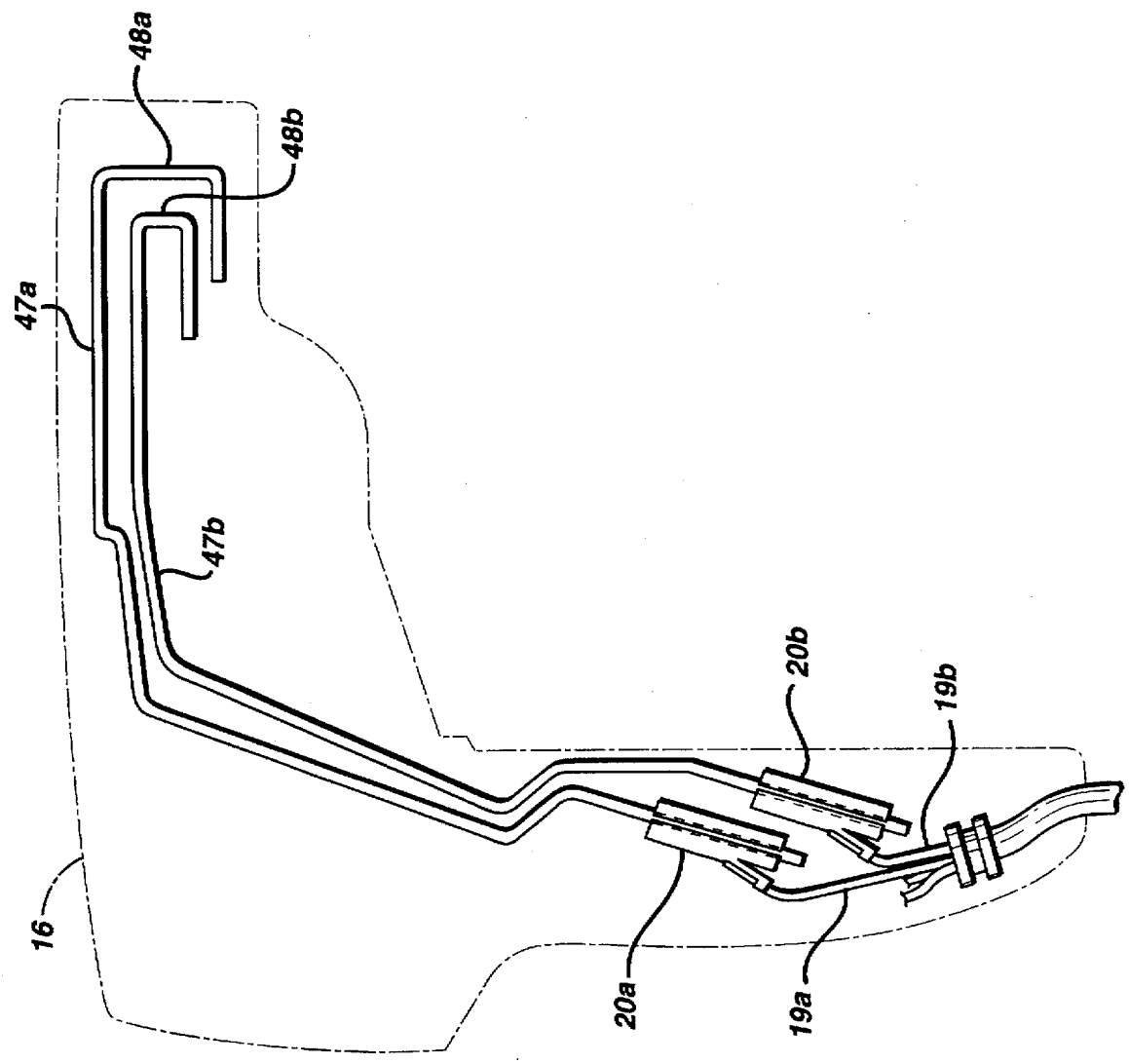
FIG. 8 is an elevational view of the inside of the left side handle portion showing the location of the wireforms and connectors used in the present invention.
Figure 13:
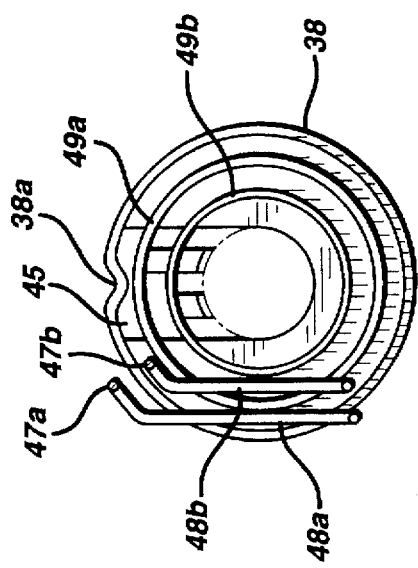
FIG. 13 is an end view of FIG. 11 showing a slight bias in the wireforms allowing for pressure of the wireforms onto their respective contact positions.
Figure 12:
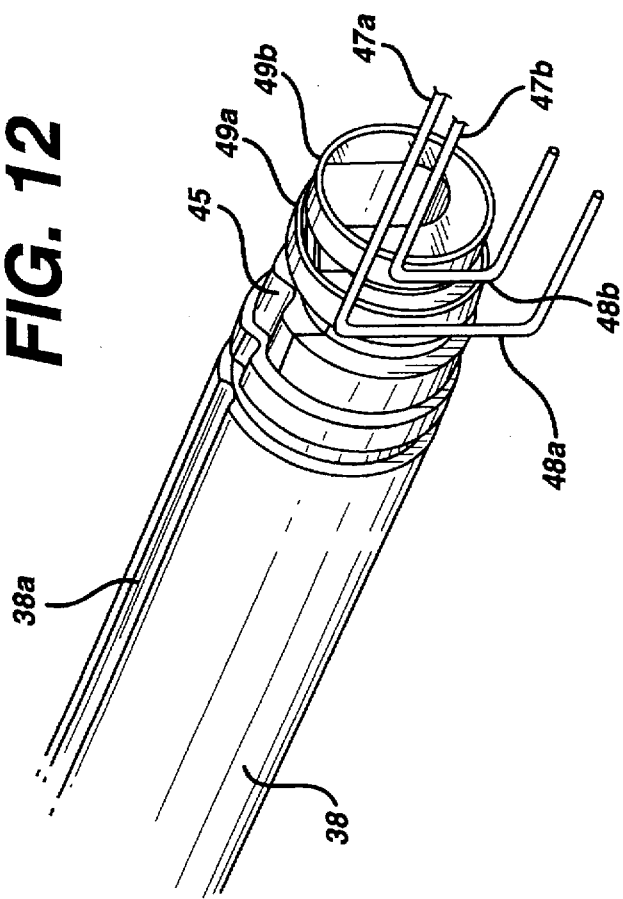
FIG. 12 is a perspective view showing the wireforms contacting their respective contact position.
Figure 16:
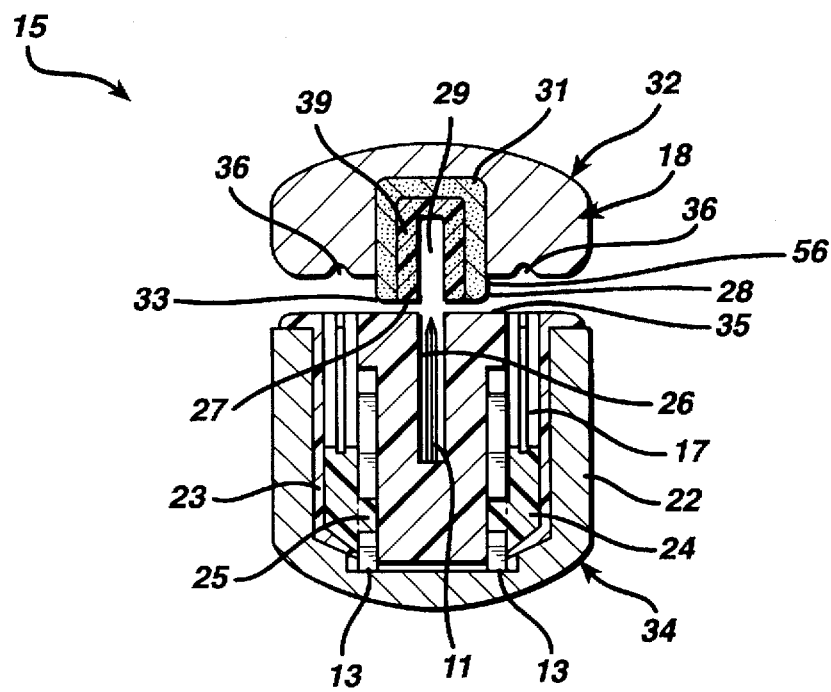
FIG. 16 is a transverse cross-sectional view taken along line 16—16 of FIG. 14.
Figure 17:
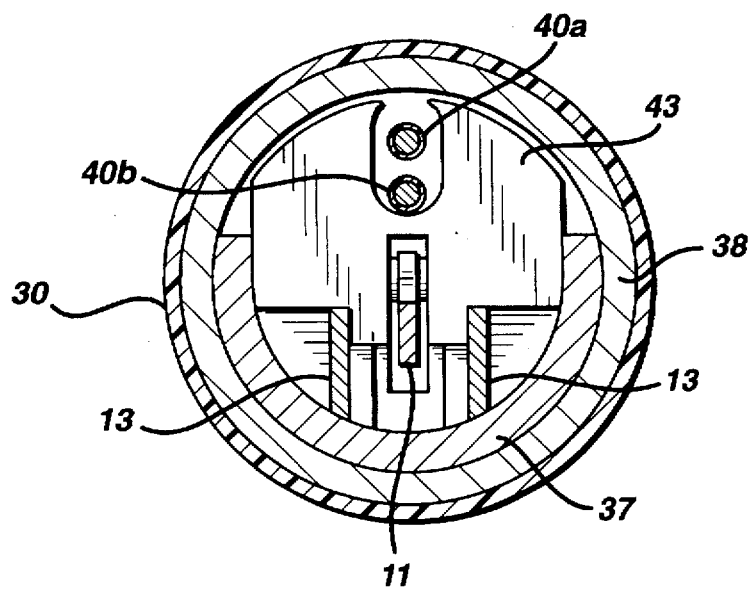
FIG. 17 is a transverse cross-sectional view taken along line 17—17 of FIG. 14.

Referring now to FIGS. 1–18 there is illustrated an instrument of the present invention. An endoscopic linear cutting and stapling instrument 10 is shown having a housing 16 coupled to a sheath 30 with a lumen extending therethrough and an end effector 15 extending from the distal end of the sheath 30. The end effector 15 comprises first and second elements which are comprised of interfacing jaw members 32, 34. Jaw member 32 is movably secured to jaw member 34. The housing 16 has a clamping trigger 12 for closing jaw members 32, 34, an electrical switch detente arm 58 and electrical switch contacts 67a, 67b, coupled to an electrical switch 59 for energy supply to heating element 39, and a firing trigger 14 for advancing the cutting element 11 through tissue and wedge 13 for applying staples 17. Jaw members 32, 34 are shown in an unclamped position in FIG. 1; in a clamped position prior to application of coagulating heat energy and prior to cutting and stapling in FIG. 2; in a clamped position after application of coagulating heat energy and prior to cutting and stapling in FIG. 3; and in a clamped position after cutting and stapling in FIG. 4.

Jaw member 32 comprises an anvil 18, surface 33 which substantially faces an inner surface 35 of jaw member 34 and a heating element 39 forming a U-shape on the surface 33. The heating element 39 comprises two bars 27, 28 extending substantially along the length of the inner surface 33 and joined at the distal end of the surface 33 of jaw member 32. The heating element 39 is comprised of a positive temperature coefficient material ("PTC material"). The heating element 39 is coupled to an electric energy source 70 to which causes the heater material to heat. The heating element 39 in this embodiment is surrounded by a heat conducting material 56 e.g., aluminum or a heat conductive plastic, which provides a gradient of heat in tissue in contact with the material 56. Of course, various materials and methods may be used to obtain a desired heat gradient in various alternative embodiments of the invention.

As the PTC material heats, the electrical impedance increases. The electrical energy source is preferably a constant voltage source. Thus, the PTC material becomes power limiting when the temperature rises above a desired level and thus the impedance rises above the desired level. If a PTC material is used, it is preferable to use a constant voltage source. The electrical characteristics of the heating thus may be sensed to indirectly sense tissue temperature.

Alternatively, the electrical characteristics of the heater can be sensed to indirectly measure tissue temperature or other properties such as heat capacity of tissue. Temperature measuring devices or sensors such as thermocouples, RTD's (resistive thermal devices), thermistors, and the like may be embedded at strategic locations, particularly in the end effector, to sense temperatures throughout the device. The delivery of heat may be controlled in response to feedback from these devices.

The bars 27, 28 are separated by a knife channel 29 extending longitudinally through the middle of the jaw member 32. Pockets 36 located on anvil 18 for receiving staple ends are located along the inner surface 33, along the length and outside of bars 27, 28, to form a row of staples on each side of element 39.

Jaw member 34 comprises a cartridge channel 22 and a cartridge 23 releasably inserted into the cartridge channel 22. The cartridge 23 includes a track 25 for wedge 13, a knife channel 26 extending longitudinally through the center of the cartridge 23, a series of drivers 24 extending into the track 25 and staples 17 arranged in two sets of single rows.

The sheath 30 is formed of an insulative material and has a closure tube 38 extending through its lumen. The closure tube 38 acts to close jaw members 32, 34 towards each other as the closure tube 38 is advanced. A channel retainer 37a extends from the proximal end of the closure tube 38 and is secured to channel 37 which there extends distally through the remainder of the closure tube 38 to form jaw member 34. The channel 37 includes cartridge channel 22 extending distally from the closure tube 38.

The body 16 has a clamping trigger 12 for advancing the closure tube 38 to close the jaws 32, 34 towards each other engaging tissue therebetween. Rotation of the clamping trigger 12 causes the closure tube 38 to advance co-axially through the sheath 30 over a camming surface 32a of jaw 32 to close the jaws 32, 34 onto tissue situated between the jaws 32, 34.

The channel retainer 37a guides co-axial movement of a drive rod 41 within the channel 37. The drive rod 41 is advanced by the rotation of the firing trigger 14 as described in more detail below. The driving rod 41 is coupled on its distal end to a block 43. The block 43 is coupled to a cutting means 11 and a staple driving wedge 13, which the drive rod 41 advances by way of the block 43 into the end effector 15. A wedge guide 46 is used to guide wedge 13 into track 25. Jaw member 32 is secured by way of the channel 37 to the jaw member 34.

When the drive rod 41 advances the cutting element 11, the cutting element 11 advances through the knife channel 26 in between the bars 27, 28 to cut tissue engaged by jaws 32, 34 when the tissue has been cauterized. Thus, the cut line is medial to the coagulation lines formed by the bar electrodes 27, 28. The drive rod 41 simultaneously advances the block 43 and thus the wedge 13 which drives the drivers 24 into the staples 17 causing the staples 17 to fire through tissue and into the pockets 36 of the anvil 18. Staples 17 are applied in single longitudinal rows on each side of the cutting element 11 as the cutting element 11 cuts the tissue.

A knob 44 located on the distal end of the body 16 rotates the closure tube 38, channel retainer 37a, channel 37 and end effector 15 which are directly or indirectly coupled to the knob 44 so that the knob 44 may be used for rotational placement of the end effector jaws 32, 34. The knob 44 includes a peg (not shown) which fits into and engages indentation 38a closure tube 38. Closure tube 38 is fitted at its proximal end, into the housing 16.

Electrical energy is supplied to the element 39, first and second electrical connections 39a, 39b located on the proximal ends of bars 27, 28. These connections receive electrical energy as described below. The supply 70 is user controlled by way of switch 59 located in the housing 16 or by footswitch or other switching means. Wires 19c, 19d extend from switch 59 to a controller included with the generator 70.

Wires 19a and 19b extend into the body 16 of the instrument and deliver energy to connections 39a, 39b respectively. Wires 19a, 19b are coupled to low impedance contact elements 20a, 20b respectively and contact elements 20a, 20b are coupled to wireforms 47a, 47b respectively. Wireforms 47a, 47b are exposed at their distal ends 48a, 48b. Wireforms 47a and 47b are biased respectively towards contact rings 49a, 49b located on the proximal end of channel retainer 37a, so as to make electrical contact with the ring 49a and ring 49b respectively.

Wire 19a delivers electrical current to the first electrical connection 39a of heating element 39 by way of first wire form 47a which contacts electrically conductive contact ring 49a which electrically coupled to wire 40a extending through closure tube 38 to element 39b.

Wire 19b delivers electrical current to the second electrical connection 39b of heating element 39 through second wire form 47b which contacts contact ring 49b coupled to wire 40b extending through the closure tube 38 to the connection 39b.

The contact rings 49a, 49b permit the knob 44 to rotate while contact is maintained between rings 49a, 49b, and wireforms 47a, 47b, respectively. The rings 49a and 49b are electrically insulated from each other.

Wires 40a, 40b extend through seal 45 which fits into channel retainer 37a, which fits into closure tube 38.

Clamping trigger 12 includes gear teeth 12a which movably engage with teeth 66b of yoke 66. Yoke 66 is coupled on its distal end to the closure tube 38. When clamping trigger 12 is actuated, the gear teeth 12a engage with teeth 66b in yoke 66 causing the yoke 66 to advance distally. Closure tube 38 closes jaws 32, 34 as it advances over camming surface 32a of jaw 32.

The switch 59 is rotated to switch on electrical energy to be supplied to the heating element 39. When the switch 59 is rotated, detente protrusion 59a on the switch 59 hooks under detente protrusion 58a on detente arm 58, preventing the switch 59 from deactivating electrical energy to the heating element 39 unless the switch 59 is manually rotated back to its original position. The electrical energy may also be turned off electrically if, for example, the impedance of the PTC material of the heating element rises above a preset value, indicating the temperature has reached a desired limit.

Switch 59 has a moveable contact 67a and a stationary contact 67b. The moveable contact 67a rotates with switch 59 to contact stationary contact 67b when switch is on. A signal is supplied to the generator 70 through wires 19c, 19d coupled to stationery contact 67b and moveable contact 67a, respectively.

Ledge 60a of release button 60 is engaged with the proximal end of the yoke 66 adjacent step ledge 66a on proximal end of yoke 66. When the yoke 66 is advanced by the clamping trigger 12, the ledge 60a rotates down behind proximal end of yoke 66, thereby preventing yoke 66 from retracting until release button 60 has been pressed. Thus the jaws 32, 34 will remain in a closed position until a user releases the jaws 32, 34 with release button 60.

The switch 59 includes fingers 59c which sit just above proximal end of yoke 66. The ledge 60a of the release button 60 fits in between fingers 59c. The switch 59 cannot be activated, i.e., rotated forward, until the yoke 66 has been advanced distally so that fingers 59c of switch 59 are free to rotate behind proximal end of yoke 66.

The switch 59 also includes a lower hook 59b which engages groove 53a of firing rack 53. Firing rack 53 includes gear teeth 53b which are engaged by gear teeth 14a of firing trigger 15. The firing rack 53 is coupled on its distal end to pinion gear 54 which in turn engages the drive rod 41.

When the firing trigger 14 is pulled, the fire rack 53 is advanced distally to rotate pinion 54 which advances the driving rod 41 distally to actuate the cutting element 11 and to drive staples 17 into tissue engaged by the end effector 15.

The firing rack 53 cannot advance however until the lower hook 59b of the switch is disengaged from the groove 53a of the firing rack 53. This occurs only when the switch has been activated.

Thus, the presently described device includes a lockout device or devices for preventing application of heating energy, staples or knife actuation until the jaws 32, 34 have been closed. The lockout device(s) require the proper sequence is followed as illustrated in FIGS. 1-4, i.e, jaw closure, followed by application of heating energy, followed by staple application and cutting element actuation. It also provides a detented switch so that electrical energy is continuously applied until the switch 59 is manually released or until the electrical energy is switched off, e.g., by a feedback control signal to the generator 70.

The closure trigger 12 and firing trigger 14 are interlocked and a spring 57 is mechanically coupled to both triggers 12, 14.

When tissue is engaged between clamped jaw members 32, 34, and heating energy has been applied, the firing trigger 14 located on housing 16 may be actuated to advance a cutting element 11 through the engaged tissue to cut the tissue. Simultaneously, when the firing trigger 14 is actuated, the wedge 13 is advanced through the track 25 causing the drivers to 24 to displace towards the staples 17, thereby driving the staples 17 through tissue and into anvil pockets 36.

In one embodiment, the cartridge provides multifire stapling capabilities by having single rows of staples, as opposed to the convention double row of staples of the cartridges in the laparoscopic stapling and cutting devices presently in use. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. The device of the present may however, if desired, include double, triple, etc., staple rows. Also, in a further embodiment, no staples are required and the coagulation lines provide the necessary hemostasis or tissue welding effect. A cartridge is defined herein to mean a staple containing mechanism.

A preferred embodiment of the present invention includes a feedback system designed to indicate when a desired or predetermined tissue effect has occurred. An audible, visible, tactile, or other feedback system may be used to indicate when sufficient cauterization has occurred at which point the heating energy may be turned off. In a particular embodiment, the feedback system measure one or more electrical parameters of the system, e.g., the electrical impedance of the PTC material of the heating element, to determine e.g., a coagulation complete condition.

Using such a feedback system, after the heating energy is turned off, the cutting means 11 is advanced and the staples 17 are fired using the firing trigger 14.

Several variations of this invention have been described in connection with specific embodiments involving endoscopic cutting and stapling. Various heating devices may be used to provide heat to tissue such as, for example, an NTC material or an inductive heating device, etc. Preferably a constant current source is used with an NTC material. Various temperature control means may be used as well. Also, various tissue status monitoring techniques may be employed, such as, for example, measurements of optical characteristics including infrared transmissivity, tissue impedance measurements, chemical sensors, etc. Naturally, the invention may be used in numerous applications where hemostasis in desired. Accordingly, it will be understood by those skilled in the art that various changes and modifications may be made in the invention without departing from its scope, which is defined by the following claims and their equivalents.

What is claimed is:

1. A surgical instrument comprising:

a shaft having a distal end;

an end effector located at the distal end of the shaft, comprising:

a distal end;

a cutting element movable in a cutting path to form a cutting line;

first and second elements comprising first and second opposed tissue contacting surfaces respectively, said surfaces moveable relative to each other from an open, spaced-apart position for positioning tissue therebetween, to a closed position for approximating the tissue, at least a portion of one of said tissue contacting surfaces comprising a heating element wherein said heating element is adapted to transmit energy to tissue engaged by said end effector, said heating element comprising:

a first elongated bar of a positive temperature coefficient material arranged on a first side of said cutting line; and a second elongated bar of a positive temperature coefficient material arranged on a second side of said cutting line.

2. The surgical device of claim 1 further comprising a longitudinal axis extending proximally to distally with respect to said end effector wherein said first and second elongated bars comprise an elongated element extending longitudinally with respect to said axis.

3. The surgical instrument of claim 1, wherein said first and second elongated bars are arranged in a substantially parallel manner with respect to each other.

4. The surgical device of claim 1 wherein said end effector further comprises:

at least one fastener and at least one applier adapted to apply said at least one fastener through tissue.

5. The surgical device of claim 1 wherein said end effector further comprises:

at least one staple and at least one driver adapted to drive said at least one staple through tissue.

6. The surgical instrument of claim 1 wherein said first and said second elongated bars are covered by a heat conducting material.

* * * * *